Aug. 9, 1960 G. MERRILL Plant Pat. 1,966

PEACH TREE

Filed April 14, 1959

WITNESS

Addison E. Avery

INVENTOR

Grant Merrill

HUEBNER & WORREL

BY Richard M. Worrel

ATTY.

United States Patent Office

Plant Pat. 1,966
Patented Aug. 9, 1960

1,966

PEACH TREE

Grant Merrill, P.O. Box 392, Red Bluff, Calif.

Filed Apr. 14, 1959, Ser. No. 806,414

1 Claim. (Cl. 47—62)

The present invention relates to a peach tree and more particularly to a new and distinct variety thereof broadly characterized by bearing highly colored, yellow firm fleshed, freestone peaches which ripen at approximately the same time as the unpatented Elberta variety.

Because of rich soil and favorable climatic environment prevailing in most of the commercial peach farming areas of California, the peach trees tend to produce rank growth and dense shade resulting in serious impairment of the coloring of the fruit. Inasmuch as most fruits rely on eye appeal for their sales, color impairment is highly undesirable. A primary object of the plant breeding procedures which have resulted in the development of this new peach variety has been to achieve a highly colored red peach which maintains its color and firmness even under conditions of rank growth and dense shade.

Another object has been to provide a new peach variety which produces fruit of satisfactory size without excessive pruning or thinning.

A collateral object has been to produce a new peach variety characterized by moderate but consistent fruit set, minimizing pruning and thinning requirements without being subject to irregular production.

Another object has been to provide a peach tree of the character described which is vigorous and healthy but of medium size so as to be susceptible to picking without excessively tall ladders and yet be of sufficient size to produce satisfactory yields when planted the usual commercial distances.

Further objects and advantages will become apparent in the subsequent description in the specification.

Figures 1, 2:
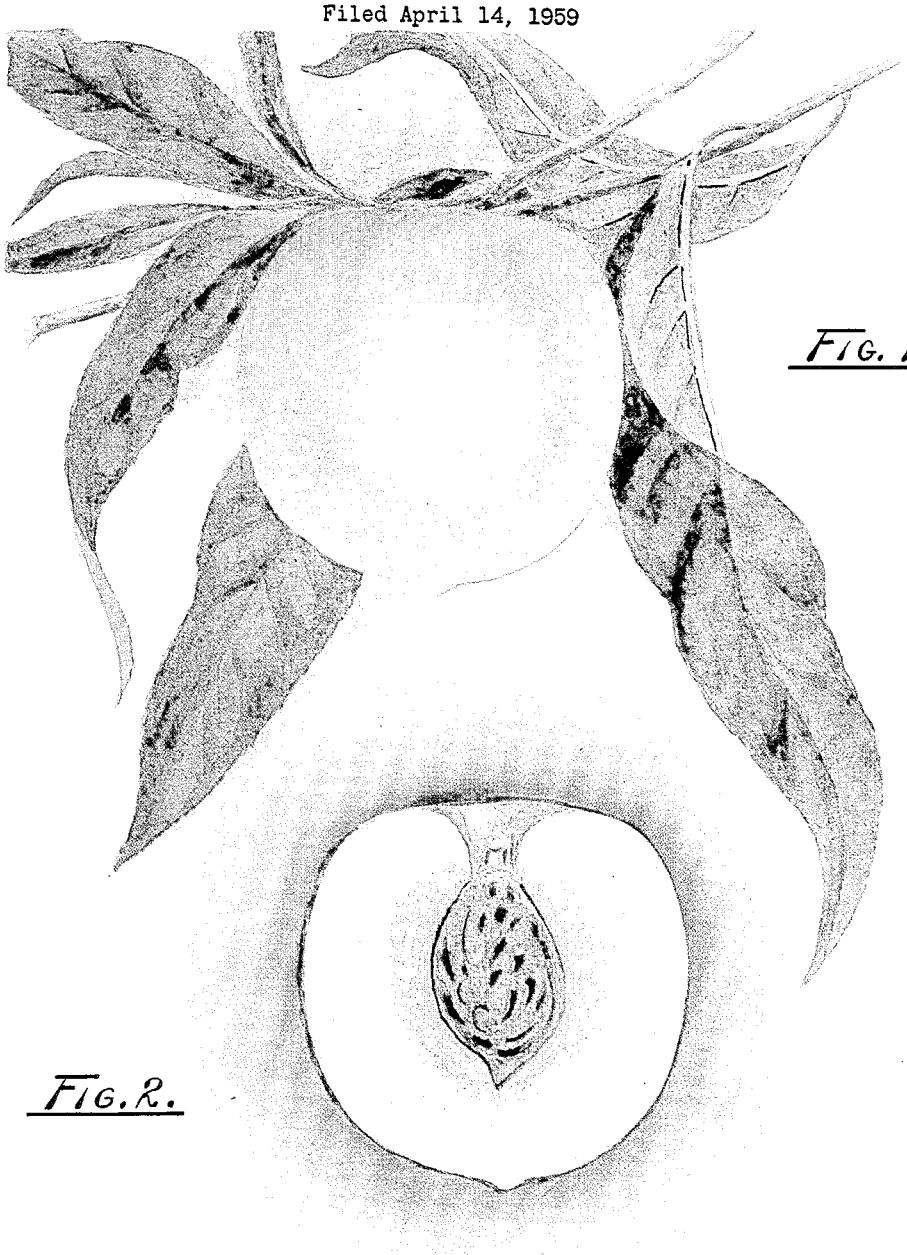
Fig. 1 is a water color painting of a characteristic fruit bearing twig of the subject peach tree having leaves and a mature peach thereon.
Fig. 2 is a water color painting showing a characteristic fruit of the subject peach tree divided on its suture plane to reveal flesh coloration and showing a pit in place therein.

The most distinctive characteristic of the instant variety of peach tree is that its fruit generally has more red on its skin surface, and is firmer fleshed than other commercial freestone peaches ripening at the same time in the San Joaquin and the Sacramento Valleys of California and specifically its fruit has more red on its skin surface and is firmer fleshed than the Merrill Fortyniner (unpatented) and the J. H. Hale (unpatented) which ripen about the same time.

The instant variety most nearly resembles the Merrill Fortyniner (unpatented), one of its parents, but is an improvement thereon in that it has more red on the skin of the fruit, has a larger and more productive tree, blooms a few days earlier and has more globular fruit. The Fortyniner tends to produce fruit having a "neck" or tapering somewhat toward the stem end. The present variety does not have this tendency, producing more spherical fruit. It blooms a few days earlier than the Fortyniner demonstrating a lower chilling requirement, adapting it to successful production in areas having warmer winters.

This new variety of peach was produced by me on my breeding farm near Red Bluff, Tehama County, California. Seeds from J. H. Hale (unpatented) growing next to Merrill Fortyniner (unpatented) were planted. Since the variety resembles Merrill Fortyniner (unpatented) in many of its characteristics. It is believed that the cross is J. H. Hale (unpatented) crossed with Merrill Fortyniner (unpatented). In August 1955, the resulting seedlings fruited and the subject variety was selected as being superior to other varieties ripening at that season. In March 1957, several Merrill June (Plant Patent No. 869) trees growing on my farm near Lamont, Kern County, California were grafted to scions of this seedling and in July 1958 the resultant trees and their fruit were observed to be identical with the original seedling.

Referring more specifically to the pomological characteristics of this new and distinct variety of peach tree, the following have been observed under the ecological conditions prevailing at my farm near Red Bluff, California. All major color plate identifications are by reference to Maerz and Paul Dictionary of Color.

*Tree*

Shape: Medium large, vigorous, neither upright nor spreading, but average in shape, productive.

Trunk: Medium stocky, medium shaggy, grey in color.

Branches: Larger branches greyish in color and shaggy, smaller branches smoother and brown to reddish brown. Lenticels—medium in quantity, medium size.

Leaves: (Selected from midportion of vigorous unbranched terminal shoot 18" to 24" long.)

*Length.*—6½" to 8¾". Average, 7⅝".

*Width.*—1⅜" to 1⅝". Average, 1½".

*Form.*—Large size, lanceolate, tip acuminate, medium thick.

*Color.*—Top of leaf medium yellowish green (22–L–7 plus yellow). Under side, lighter green (21–L–6). Heavy under midrib lighter green (18–J–1).

*Class.*—(Meader and Blake Proceedings: Am. Soc. Hor. Sc., vol. 37, page 206).—2 to 3. Width—length ratio—.20. Apex angle (1" from tip)—21° to 33°; average, 28°. Base angle (½" from petiole)—63° to 86°; average, 74°.

*Margin.*—Crenate.

*Petiole.*—Medium length, medium thickness.

*Stipules.*—On young leaves, falling off early.

*Glands.*—Usually two, sometimes more, opposite and alternate, medium size, reniform, yellowish green, sometimes brown on older leaves.

Flower buds: Medium size, medium length, plump, free, pubescent.

Flowers: Bloom relatively early; slightly earlier than July Elberta (Plant Patent No. 15), small, dark pink color.

*Fruit*

Maturity when described, firm ripe.

Size: Variable, large.

*Axial diameter.*—3" to 3¼". Average, 3⅛".

*Transverse in suture plane.*—3" to 3½". Average, 3 5/32".

*At right angles to suture plane.*—2¾" to 3¼". Average, 3 3/32".

Form: Unsymmetrical, globose with some slightly obovate.

*Suture.*—A conspicuous line, sometimes inconspicuous, extends from base to beyond, but discontinues at apex, with slight marked depression beyond pistil point, some ridge usually present.

*Ventral surface.*—Rounded.

*Cavity.*—Variable, usually somewhat flaring, less so on riper fruit; elongated in suture plane with suture showing usually on both sides. Depth, 9/16" to ¾". Width, variable, ⅝" to 1¼". Markings—yellow under color; brush, none to entire surface, except where stem has touched the fruit.

*Base.*—Retuse.

*Apex.*—Rounded to retuse, sometimes truncate; pistil point apical.

*Stem.*—Length ½" to ¾". Diameter, ⅛". Adheres to stone in some instances.

*Skin.*—Medium thick, medium tough, tenacious to flesh.

*Tendency to crack.*—None.

*Color.*—Light yellow (9–L–5) to darker yellow (11–G–10), with lighter red blush (4–K–11) to darkest red (7–L–6). Down scant, short, does not roll up when rubbed.

Flesh:

*Color.*—Light yellow (9–L–4) to darker yellow (10–L–7) with red near the stone (5–L–6).

*Surface of pit cavity.*—Red.

*Amygdalin.*—Moderate.

*Juice.*—Moderate.

*Texture.*—Firm, fine.

*Fibers.*—Moderate in amount, tender.

*Ripens.*—Fairly evenly but some tendency to ripen first at the base.

*Flavor.*—Mild, delicate.

*Aroma.*—Moderate.

*Eating quality.*—Good.

Stone: Free, adheres to flesh occasionally near stem end on ventral edge, fibers usually lacking, but where present are long.

*Size.*—Medium to large. Length, 1½" to 1¾"; average, 1⅝". Width, 1 1/16" to 1⅛"; average, 1 3/32". Thickness, ¾" to 15/16"; average 13/16".

*Form.*—Obovate, tip acuminate.

*Base.*—Variable, some straight, some oblique.

*Hilum.*—Oval.

*Apex.*—Acuminate.

*Sides.*—Some equal and some unequal.

*Surface.*—Irregularly furrowed near ventral edge and apex; pitted toward base and near dorsal edge with considerable variation. Pits variable in number and shape.

*Ventral edge.*—Moderately thick, without wing.

*Dorsal edge.*—Grooved and ridged, interrupted.

*Color.*—Brown (7–C–11) with some tinges of red especially near stem end.

*Tendency to split.*—Little.

Use: Fresh market local and long distant.

Keeping quality: Good.

Shipping quality: Good:

It has further been observed that the fruit is relatively free of split pits and growing cracks, hangs on the tree well in spite of windy conditions resists skin tearing during picking, packing and other handling, is subject to a minimum of skin cutting by the stems because of their relatively short length, possesses a high ascorbic acid (vitamin C) content demonstrated by color retention of the flesh when exposed to the air.

Although the new variety of peach tree possesses the described characteristics under the growing conditions prevailing throughout most of the commercial peach producing areas of California, having been first observed near Red Bluff, California at the northern end of the Sacramento Valley and later confirmed by observation of the same variety near the southern end of the San Joaquin Valley of California approximately four hundred miles farther south, it is to be understood that variations of the usual magnitude in characteristics incident to growing conditions, fertilization, pruning, thinning, and pest control are to be expected.

Having thus described my new peach tree, what is claimed as new and desired to be secured by Letters Patent is:

A new and distinct variety of peach tree, substantially as illustrated and described, characterized by highly colored, firm yellow fleshed, freestone peaches, ripening with the unpatented Elberta variety but distinguished therefrom and from fruit of its suspected parent, the unpatented Fortyniner, by distinctly more red coloration of the skin and more symmetrically globular shape.

No references cited.